United States Patent [19]

Asano et al.

[11] Patent Number: 4,850,220
[45] Date of Patent: Jul. 25, 1989

[54] APPARATUS FOR MEASURING AMOUNT OF ULTRAFILTRATE AND CONCENTRATION OF RECEIVING SOLVENT IN DIALYSIS

[76] Inventors: Kiyokazu Asano, No. 10-10, 2-chome, Tokura, Mishima-shi, Shizuoka, Japan; Fumitaka Asano, Urawa Park Haitsu 8-503, No. 33-8, 2-chome, Harayama, Urawa-shi, Saitama, Japan

[21] Appl. No.: 116,969

[22] Filed: Nov. 5, 1987

[30] Foreign Application Priority Data

May 18, 1987 [JP] Japan .............................. 62-120846

[51] Int. Cl.$^4$ .............................................. G01F 1/66
[52] U.S. Cl. .................................. 73/196; 73/61.1 R; 73/861.28; 210/195.2
[58] Field of Search ...................... 73/196, 195, 861.27, 73/861.28, 61.1 R, 861.31; 210/647, 195.2

[56] References Cited

U.S. PATENT DOCUMENTS

| | | | |
|---|---|---|---|
| 2,991,650 | 7/1961 | Katzenstein et al. | 73/861.28 |
| 3,555,899 | 1/1971 | Miaki Yamamoto et al. | 73/861.27 |
| 4,159,647 | 7/1979 | Paulson et al. | 73/861.28 |
| 4,195,517 | 4/1980 | Kalinoski et al. | 73/861.27 |
| 4,227,407 | 10/1980 | Drost | 73/861.28 |
| 4,308,754 | 1/1982 | Pedersen et al. | 73/861.28 |
| 4,409,847 | 10/1983 | Magori | 73/196 |
| 4,454,767 | 6/1984 | Shinkai et al. | 73/861.28 |
| 4,480,486 | 11/1984 | Meisser et al. | 73/861.28 |
| 4,610,167 | 9/1986 | McShane | 73/861.28 |
| 4,693,319 | 9/1987 | Amemiya | 73/861.27 |

FOREIGN PATENT DOCUMENTS 824537 12/1959 United Kingdom .
1200349 7/1970 United Kingdom .

Primary Examiner—Herbert Goldstein
Attorney, Agent, or Firm—Browdy and Neimark

[57] ABSTRACT

An apparatus for measuring an amount of ultrafiltrate produced in a hemodialyzer and a concentration of a receiving solvent employed in the hemodialyzer by means of an ultrasonic wave, comprises: an ultrasonic vibrator; each of an inlet and an outlet flow-rate measuring parts provided with an input flow channel and an output flow channel; and a reflector interposed between the inlet and the outlet flow-rate measuring parts to permit only the ultrasonic wave to pass therethrough, the reflector reflecting the ultrasonic wave so that the ultrasonic wave issued from one of the inlet and the outlet flow-rate measuring parts is directed to the other.

3 Claims, 1 Drawing Sheet

APPARATUS FOR MEASURING AMOUNT OF ULTRAFILTRATE AND CONCENTRATION OF RECEIVING SOLVENT IN DIALYSIS

BACKGROUND OF THE INVENTION

1. Field of the Invention:

The present invention relates in particular to hemodialysis: It is an apparatus for measuring an amount of ultrafiltrate produced in the hemodialysis and a concentration of the receiving solvent employed in the hemodialysis by the use of ultrasonic waves.

2. Description of the Prior Art:

In recent years, in the field of hemodialysis, the performance of hemodialyzers is remarkably improved. As a result, there is a strong demand for methods that can measure the amount of ultrafiltrate or water removed from blood after having been dialyzated. In the majority of cases, the flow rate of the receiving solvent employed in the hemodialyzer reaches an amount of 500 ml per minutes while that of the ultrafiltrate produced in the hemodialyzer reaches up to only several percent of 500 ml, which reaches that the amount of the ultrafiltrate is measured with accuracies of up to 0.1% of 500 ml.

The conventional methods for measuring the amount of ultrafiltrate produced in the hemodialyzer can be classified into three categories. All of these conventional methods, however, suffer from its inherent defects as follows. In the first method, a pair of fixed-volume chambers is employed, each of which is separated into two rooms by a movable partition. Through this input-flo rate to the hemodialyzer is kept equal to an output-flow rate from the same by the use of a selector valve, while ultrafiltration is forcibly conducted by the use of other means. Although this method is excellent in accuracy, it is too complex and can be conducted only by the use of an apparatus provided with many expensive components. In addition, the selector valve tends to be worn out quickly because of excessive operation, which deteriorates the accuracy of the apparatus. However, it is hard to detect the deterioration of the accuracy. Next, in the second method, both an input circuit and an output circuit of the hemodialyzer are temporarily shut off in order that the pressure across a membrane and the amount of ultrafiltrate are determined, whereby the amount of ultrafiltrate produced at a time when these input and output circuits are open is calculated on the basis of the pressure across the membrane and the relationship between the above determined values. Although the second method is simple in construction to make it possible to determine the amount of ultrafiltrate, its accuracy is reduced when it is conducted by the use of a high-performance hemodialyzer or a specialized hemodialyzer. In addition, since the conditions of the moment when the circuits are shut off differ from those of the moment when the calculation is conducted and change at each hour of operation, the thus determined values are poor in reliability. Lastly, in the third method, both an input and an output flow rates in the hemodializer are directly determined by means of a flow meter to find differences in flow rate therebetween, so that the amount of ultrafiltrate is determined on the basis of such differences in flow rate. Although this third method is basic, it is seldom employed in practical use, because it is hard to obtain a flow meter with a sufficient accuracy in use and an outlet side of the hemodializer is seriously soiled with dirt. In this connection, Japanese Patent Publication No. 59-10227 discloses an apparatus provided with a flow meter which is poor in accuracy and is changed over in use to make it possible that its inlet circuit also serves as an outlet circuit thereof, and vice versa. Such change-over use of the circuits seriously contaminates the apparatus, which in turn makes it necessary to disinfect the apparatus frequently.

On the other hand, in determining a concentration of the receiving solvent employed in the hemodialyzer, the electrical conductivity of the receiving solvent is generally determined by means of metallic or carbon electrodes. In recent years, there is an incessant growth in demand for solutions of bicarbonates which might serve as the receiving solvents in the hemodialyzer, because the solutions of bicarbonates do not adversely affect the patient substantially. The receiving solvent of this type has a problem in that it tends to produce carbonates deposited on the electrodes when the composition of the receiving solvent changes, the carbonates being an electrically insulating materials. Consequently, it is hard to control the concentration of the receiving solvent of this type, which leads to difficulty in giving the alarm for an abnormal concentration of the receiving solvent. Such abnormal concentrations of the receiving solvent in use are very dangerous to for the patient.

SUMMARY OF THE INVENTION

Any of the conventional method for determining an amount of the ultrafiltrate and a concentration of the receiving solvent has the problems described above, and therefore, it is not suited for practical use. Accordingly, it is an object of the present invention to provide an apparatus for measuring the amount of ultrafiltrate produced in hemodialysis and the concentration of the receiving solvent employed in the hemodialysis so as to resolve the above mentioned problems.

It is another object of the present invention to provide an apparatus for measuring the amount of the ultrafiltrate an appartus which is capable of directly determining both an input amount and an output amount of the receiving solvent with the use of a simple construction without using any expensive and expendable parts for continuous determination of the amount of the filtrate, and without reducing its measuring accuracy in an condition, the apparatus being compact in construction as a whole.

It is a further object of the present invention to provide an apparatus for measuring a concentration of the receiving solvent, whereby the apparatus is not adversely affected even when carbonates are deposited in the receiving solvent, and, therefore capable of ensuring safety in use.

Other objects, features and advantages of the present invention will be apparent from the following description.

DESCRIPTION OF THE PREFERRED EMBODIMENTS

The preferred embodiments of the present invention will be hereinbelow described in detail with reference to the accompanying drawings.

Figure 1:
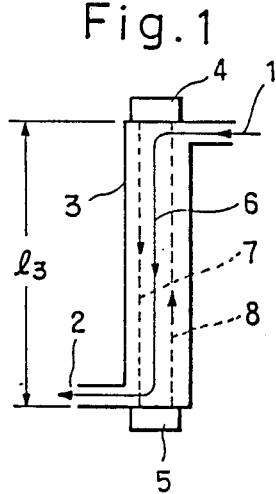
FIG. 1 is a schematic view illustrating a principle of an ultrasonic flow meter.

First, a principle of a method for measuring a flow rate of the receiving solvent of the hemodialyzer by the use of ultrasonic waves will be described with reference to FIG. 1. The receiving solvent to be measured is introduced into a flow-rate measuring portion 3 of an apparatus from an input side 1 thereof and passes through the flow-rate measuring portion 3 at a flow velocity of $v_6$ so as to be issued to an output side 2. Under such circumstances, an ultrasonic vibrator 4 issues an ultrasonic wave which is propagated through the flow-rate measuring portion 3 of the apparatus at a velocity of $V_7$ represented by the following equation (1):

$$V_7 = V + v_6 \tag{1}$$

where: V is a velocity of the ultrasonic wave passing through the receiving solvent when it is kept stationary.

Based on the equation (1), a time $T_{4 \to 5}$ taken for the ultrasonic wave to be propagated from the ultrasonic vibrator 4 to an ultrasonic vibrator 5 is represented by the following equation (2):

$$T_{4 \to 5} = l_3/V_7 = l_3/(V + v_6) \tag{2}$$

where: $l_3$ is a distance between the ultrasonic vibrators 4 and 5.

In the same manner as above, a time $T_{5 \to 4}$ taken for the ultrasonic wave to be propagated from the ultrasonic vibrator 5 to the ultrasonic vibrator 4 is represented by the following equation (3):

$$T_{5 \to 4} = l_3/V_8 = l_3/(V - v_6) \tag{3}$$

where: $V_8$ is a velocity of the ultrasonic wave issued from the ultrasonic vibrator 5 to the ultrasonic vibrator 4 in the flow-rate measuring portion 3 against the flow of the receiving solvent.

Based on the equations (2) and (3), a difference in time $\Delta T$ is represented by the following equation (4):

$$\Delta T = (2l_3 \times v_6)/((V + v_6)(V - v_6)) \tag{4}$$

Since the $l_3$ and V are known values, it is possible to determine the flow velocity $v_6$ of the receiving solvent on the basis of the equation (4) by measuring the difference in time $\Delta T$. In addition, it is also possible to know a flow rate of the receiving solvent in the flow-rate measuring portion 3 of the apparatus on the basis of a cross-sectional area of the flow-rate measuring portion 3 and the $v_6$.

Figure 2:
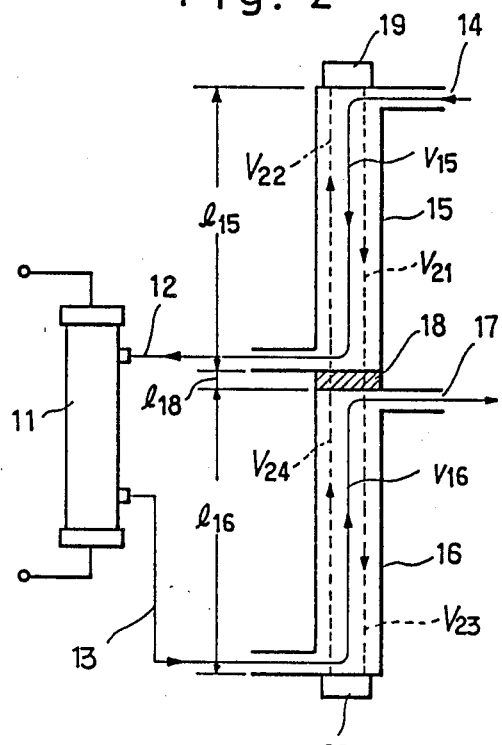
FIG. 2 is a schematic view illustrating the construction of an embodiment of the apparatus of the present invention.

Now, the apparatus of the present invention will be described in construction with reference to FIG. 2. As shown in FIG. 2, the receiving solvent employed in the hemodialyzer enters an input flow-rate measuring portion 15 of the apparatus of the present invention, which is connected to a supply of receiving solvent 14, to pass therethrough at a flow velocity of $v_{15}$, and enters a hemodialyzer 11 through its inlet opening 12, in which hemodialyzer 11 waste products and some of water are removed from blood being subjected to ultrafiltration. As a result, a volume of the receiving solvent is increased by the addition of such waste products and some water. The thus increased receiving solvent is issued from an outlet opening 13 of the hemodialyzer 11 to enter a bottom of an output flow-rate measuring portion 16 of the apparatus of the present invention, and passes therethrough at a flow velocity of $v_{16}$ so as to be issued from an outlet side 17 of the outlet flow-rate measuring portion 16 of the apparatus of the present invention. In this case, the input flow-rate measuring portion 15 is separated from the outlet flow-rate measuring portion 17 by means of a partition 18 permitting only the ultrasonic wave to pass therethrough, and is axially aligned with the outlet flow-rate measuring portion 16. In order to reduce the loss of ultrasonic energy in boundaries between the receiving solvent and the partition 18 as much as possible, the partition 18 is made of a specific acoustic impedance which is preferred to be substantially the same as that of the receiving solvent, the specific impedance being defined as the product of a density of the material and the propagation velocity of the ultrasonic wave. Consequently, the partition 18 is preferably made of medical high polymers, for example such as silicone resins, urethane and the like. It is also possible to construct the partition 18 from a thin metallic foil having a low density such as titanium foil. The inlet flow-rate measuring portion 15 of the apparatus of the present invention is equal in cross section to the outlet flow-rate measuring portion 16 of the same, so that the flow velocities of the receiving solvent in these portions 15 and 16 are kept equal to each other, provided that there is no difference in flow rates between these portions 15 and 16. In addition, in the apparatus of the present invention shown in FIG. 2, a flow direction of the receiving solvent in the inlet flow-rate measuring portion 15 is opposite to that of the receiving solvent in the outlet flow-rate measuring portion 16 through the partition 18. On the other hand, the distance $l_{15}$ is equal to the distance $l_{16}$ so that an influence exerted by the outlet flow rate of the receiving solvent on the propagation velocity of the ultrasonic wave is offset by an influence exerted by the inlet flow rate of the receiving solvent on the propagation velocity of the ultrasonic wave. In the above construction of the present invention, a difference in flow velocity of the receiving solvent between the inlet flow-rate measuring portion 15 and the outlet flow-rate measuring portion 16 can be determined by measurement of a difference between the propagation velocity in opposite directions in the apparatus of the present invention. Based on the thus obtained difference in propagation velocity of the ultrasonic wave and the cross-sectional areas of the measuring portions 15 and 16, it is possible to determine a difference in flow rate between the inlet flow-rate measuring portion 15 and the outlet flow-rate measuring portion 16 of the apparatus of the present invention, the thus obtained difference in flow rate being defined as an amount of ultrafiltrate. In hemodialysis conditions with the use of the apparatus having the above construction, it is possible to neglect influences of temperature and concentration of the receiving solvent since variations thereof are minimum.

In the apparatus of the present invention having the above construction, the amount of the ultrafiltrate will be calculated as follows. As shown in FIG. 2, when the ultrasonic wave is issued from the ultrasonic vibrator 19, such ultrasonic wave passes through the inlet flow-rate measuring portion 15 of the apparatus at a flow velocity of $V_{21}$, which is represented by the following equation (5):

$$V_{21} = V_s + v_{15} \tag{5}$$

where: $V_s$ is a propagation velocity of the ultrasonic wave in the inlet flow-late measuring portion 15 in a condition in which the receiving solvent is kept stationary in the portion 15; and $v_{15}$ is a flow velocity of the receiving solvent in the inlet flow-rate measuring portion 15 in operation.

Consequently, a time $T_{F15}$ taken for the ultrasonic wave to pass through the inlet flow-rate measuring portion 15 is represented by the following equation (6):

$$T_{F15} = l_{15}/V_{21} = l_{15}/(V_s + v_{15}) \tag{6}$$

where: $l_{15}$ is a length of the inlet flow-rate measuring portion 15 between the ultrasonic vibrator 19 and the partition 18.

On the other hand, a time $T_{F16}$ taken for the ultrasonic wave to pass through the outlet flow-rate measuring portion 16 is represented by the following equation (7):

$$T_{F16} = l_{16}/V_{23} = l_{16}/(V_s \pm \Delta V_s - v_{16}) \tag{7}$$

where: $V_{23}$ is a propagation velocity of the ultrasonic wave passing through the outlet flow-rate measuring portion 16 in operation; $v_{16}$ is a flow velocity of the receiving solvent in the outlet flow-rate measuring portion 16 in operation; and $\pm \Delta V_s$ is a difference in propagation velocity of the ultrasonic wave between the inlet 15 and the outlet 16 flow-rate portions due to differences in temperature and concentration of the receiving solvent between these portions 15 and 16.

Now, a time $T_F$ taken for the ultrasonic wave issued from the ultrasonic vibrator 19 to reach the ultrasonic vibrator 20 is represented by the following equation (8):

$$T_F = T_{F15} + T_{F18} + T_{F16} \tag{8}$$

where: $T_{F18}$ is a time taken for the ultrasonic wave to pass through the partition 18.

On the other hand, in case that the ultrasonic wave to pass through the outlet flow-rate measuring portion 16 is represented by the following equation (9):

$$T_{R16} = l_{16}/V_{24} = l_{16}/(V_s \pm \Delta V_s + v_{16}) \tag{9}$$

where: $V_{24}$ is a propagation velocity of the ultrasonic wave passing through the outlet flow-rate measuring portion 16 in operation.

In the same manner as above, a time $T_{R15}$ for the ultrasonic wave to pass through the inlet flow-rate measuring portion 15 is represented by the following equation (10):

$$T_{R15} = l_{15}/V_{22} = l_{15}/(V_s - v_{15}) \tag{10}$$

where: $V_{22}$ is a propagation velocity of the ultrasonic wave passing through the inlet flow-rate measuring portion 15.

Consequently, a time $T_R$ for the ultrasonic wave issued from the ultrasonic vibrator 20 to reach the ultrasonic vibrator 19 is represented by the following equation (11):

$$T_R = T_{R16} + T_{R18} + T_{R15} \tag{11}$$

Based on the above equations (8) and (11) as well as on the fact that the $T_{F18}$ is equal in amount to the $T_{R18}$, it is possible to determine a difference $\Delta T$ in propagation i time of the ultrasonic wave as follows:

$$\Delta T = T_R - T_F = T_{R16} + T_{R15} - (T_{F15} + T_{F16}) \tag{12}$$

Due to the addition of ultrafiltrate produced in the hemodialyzer to the receiving solvent, the receiving solvent increases in volume so that the flow rate thereof in the outlet flow-rate measuring portion 16 of the apparatus of the present invention increases by an amount of $\Delta v$, so that an equation: $v_{16} = v_{15} + \Delta v$ is obtained, which equation is substituted into the equations (7) and (9) respectively, and then into the equation (12) into which the equations (6) and (10) are also substituted to produce the following equation (13):

$$\Delta T = l_{16}/(V_s \pm \Delta V_s + v_{15} + \Delta v) + l_{15}/(V_s - v_{15}) - l_{15}/(V_s + v_{15}) - l_{16}/(V_s \pm \Delta V_s - v_{15} - \Delta v) \tag{13}$$

Since the $l_{15}$ is equal in amount to the $l_{16}$, any of the $l_{15}$ and $l_{16}$ can be represented by the same character "l" so that the equation (13) is transformed into the following equation (14):

$$\Delta T = l\,((2V_s \pm \Delta V_s + \Delta v)/((V_s \pm \Delta V_s + v_{15} + \Delta v)(V_s - v_{15})) - (2V_s \pm \Delta V_s - \Delta v)/((V_s + v_{15})(V_s \pm \Delta V_s - v_{15} - \Delta v))) \tag{14}$$

Since any of the items of $\pm \Delta V_s$, $\Delta v$ and $v_{15}$ in the equation (14) is too small in relation to the $V_s$, the equation (14) can be substantially transformed into the following equation (15), provided that any of these small items is neglected:

$$\Delta T = l(2V_s \pm \Delta V_s + \Delta v - (2V_s \pm \Delta V_s - \Delta v))/V_s^2 = 2l \times \Delta v/V_s^2 \tag{15}$$

Consequently, when the $\Delta T$ is determined, it is possible to calculate the flow velocity "$\Delta v$" of the ultrafiltrate, which has been added to the receiving solvent in the hemodialyzer on the basis of the equation (15). In this connection, since the cross-sectional areas of the flow-rate measuring portions 15 and 16 are known, it is then possible to calculate the amount of the ultrafiltrate on the basis of the above fact and the equation (15). Therefore, so long as the temperature of the receiving solvent varies within a relatively narrow range in use and the differences in temperature and concentration of the receiving solvent between the inlet 15 and the outlet 16 flow-rate measuring portions of the apparatus of the present invention are substantially negligible, it is possible to determine precisely the amount of the ultrafiltrate produced in the hemodialyzer, the amount of the ultrafiltrate being extremely small in relation to the total amount of the receiving solvent employed in the hemodialyzer. Incidentally, times taken for ultrasonic waves to pass through the receiving solvent are determined according to the conventional method for determining the propagation velocities of the ultrasonic waves, for example such as PLL method and the like. Differences in the thus determined times are processed in microcomputers to eliminate abnormal data based on interference caused by bubbles mixed into the receiving solvent and like interferences, so that the amount of the ultrafiltrate produced in the hemodialyzer is precisely determined.

Now, a method for measuring a concentration of the receiving solvent is to be described. As mentioned above, it is possible to determine the propagation velocity of the ultasonic wave by the use of the apparatus of the present invention in the process for determining the amount of the ultrafiltrate. In addition, the temperature of the receiving solvent is easily determined according to the conventional method. Consequently, based on these data such as the propagation velocity of the ultrasonic wave, the temperature of the receiving solvent, and the relationship between these data and the concentration of the receiving solvent, it is possible to calculate the concentration of the receiving solvent. Even in the case of the receiving solvent a range of temperature variation of which is relatively narrow, the relationship between the propagation velocity of the ultrasonic wave and the concentration of the receiving solvent is nonlinear. However, it is possible to calculate the concentration of the receiving solvent by means of microcomputers.

Accordingly, the apparatus of the present invention for determining the amount of the ultrafiltrate described above is capable of precisely determining the concentration of the concentration of the receiving solvent without any additional construction.

Further, since the apparatus of the present invention is not adversely affected in performance by carbonates deposited in the receiving solvent, there is no fear of malfunction. In addition, the apparatus of the present invention is excellent in safety in use and is capable of providing the apparatus for measuring the concentration of the receiving solvent at a very low cost in combination with the apparatus for measuring the amount of the ultrafiltrate.

Another embodiment of the apparatus of the present invention will be described hereinbelow with reference to FIG. 3.

Figure 3:
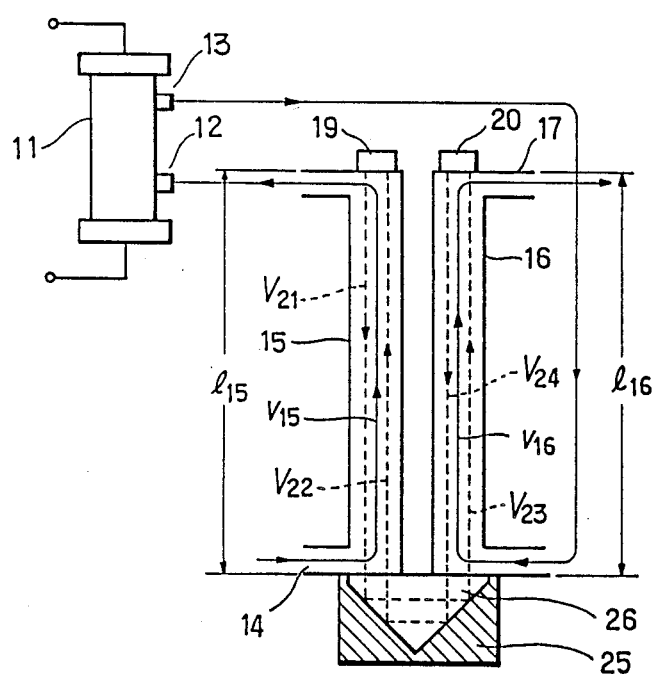
FIG. 3 is a schematic view illustrating the construction of another embodiment of the apparatus of the present invention.

As shown in FIG. 3, the apparatus of this embodiment of the present invention is provided with the inlet 15 and the outlet 16 flow-rate measuring portions each of which is provided with an inlet channel and an outlet channel. Between these measuring portions 15 and 16 is interposed a reflector 25 which prevents the receiving solvent from passing therethrough and so reflects the ultrasonic wave so that the wave which has passed through one of these measuring portions 15 and 16 is directed to the other 15 or 16. In order to make the apparatus of the present invention most compact in size and to make it easy for the bubbles produced in the apparatus of the present invention to pass through these measuring portions 15 and 16, it is preferable that the ultrasonic wave ie reflected at an angle 180° through the reflector 25, as shown in FIG. 3. Although the angle of reflection of the reflector 25, which corresponds to 180° in the above case, can be arbitrarily selected, it is not preferable to select other angles of reflection except 180°. Incidentally, in this apparatus, it is preferable for any of the inlet 15 and the oulet 16 flow-rate measuring portions to elongate its' axial length. In case that the angle of reflection of the reflector 25 is not 180°, the size of the apparatus of the present invention increases as an angle formed between the longitudinal axes of the inlet 15 and the outlet 16 flow-rate measuring portions becomes large. In the apparatus of the present invention shown in FIG. 3, such angle formed between the longitudinal axes of the inlet 15 and the outlet 16 flow-rate measuring portions of the apparatus is 0°. In case that the apparatus of the present invention is too large in size, easiness in use of the apparatus seriously deteriorates. However, in order to improve accuracy in measurement of the data, it is necessary to employ the inlet 15 and the outlet 16 flow-rate measuring portions as long as possible. In addition, although the receiving solvent generally contains fine bubbles therein, the apparatus of the present invention with the construction described above and shown FIG. 3 makes it possible that such fine bubbles contained in the receiving solvent move easily upward in each of the inlet 15 and the outlet 16 flow-rate measuring portions of the apparatus. In this embodiment of the apparatus of the present invention, as shown in FIG. 3, the ultrasonic vibrator 19 and 20 are provided in upper portions of the inlet 15 and the outlet 16 flow-rate measuring portions of the apparatus, respectively. Further, in the inlet flow-rate measuring portion 15 of the apparatus is separated from the outlet flow-rate measuring portion 16 of the same by means of the partition 26 which permits the ultrasonic wave to pass therethrough but not the receiving solvent. The ultrasonic waves issued from the ultrasonic vibrators 19 and 20 pass through the partition 26 and then reflected by the reflector 25 so as to be passed through the outlet 16 and the inlet 15 flow-rate measuring portions, respectively. The partition 26 can be made of the same material as that of the partition 18 employed in the embodiment of the present invention shown in FIG. 2. On the other hand, the reflector 25 can be made of any material capable of totally reflecting an incident ultrasonic wave. Namely, the reflector 25 can be made of suitable metallic materials such as stainless steels, aluminum and like metallic materials in which the ultrasonic wave can travel at a larger velocity than that in the receiving solvent. In the embodiment of the apparatus of the present invention shown in FIG. 3, the inlet flow-rate measuring portion 15 of the apparatus is equal in cross-sectional area to the outlet flow-rate measuring portion 16 of the same so that the flow velocity of the receiving solvent in the inlet flow-rate measuring portion 15 is kept equal to that of the receiving solvent in the outlet flow-rate measuring portion 16. In addition, with respect to the reflector 25, the receiving solvent flows in the inlet flow-rate measuring portion 15 in a direction opposite to that in the outlet flow-rate measuring portion 16, which offsets the influence exerted by the inlet flow rate of the receiving solvent on the propagation velocity of the ultrasonic wave by means of the influence exerted by the outlet flow rate of the same on the propagation velocity of the ultrasonic wave. In this case, the length $l_{15}$ of the inlet flow-rate measuring portion 15 is equal to that $l_{16}$ of the outlet flow-rate measuring portion 16. Since the apparatus of the present invention has the above construction, it is possible to obtain the difference in flow velocity of the receiving solvent between the inlet 15 and the outlet 16 flow-rate measuring portions of the apparatus by measurement of difference in propagation velocity of the ultrasonic wave in the inlet 15 and the outlet 16 flow-rate measuring portions of the apparatus. In addition, since the cross-sectional areas of the inlet 15 and the outlet 16 flow-rate measuring portions are known, it is also possible to obtain the difference in flow rate of the receiving solvent on the basis of the above fact. Namely, the apparatus of the present invention is capable of determining the amount of the ultrafiltrate produced in the hemodialyzer. In hemodialysis, since the receiving solvent varies in temperature and concentration within a very narrow range, it is possible to neglect the influences exerted by such variations on the data.

In the apparatus of the present invention described above and shown in FIG. 3, the amount of the ultrafiltrate is calculated as follows. The ultrasonic wave issued from the ultrasonic vibrator 19 passes through the receiving solvent at a propagation velocity $V_s$ in a condition in which the receiving solvent is kept stationary. Consequently, in case that the receiving solvent flows in the inlet flow-rate measuring portion 15 at a flow velocity $v_{15}$, the ultrasonic wave passes through the inlet flow-rate measuring portion 15 at a propagation velocity $V_{21}$, which is represented by the following equation (16):

$$V_{21} = V_s - v_{15} \quad (16)$$

Since the length of the inlet flow-rate measuring portion 15 is $l_{15}$, the time $T_{F15}$ taken for the ultrasonic wave to pass through the inlet flow-rate measuring portion 15 is represented by the following equation (17):

$$T_{F15} = l_{15}/V_{21} = l_{15}/(V_s - v_{15}) \quad (17)$$

On the other hand, the time $T_{F16}$ taken for the ultrasonic wave to pass through the outlet flow-rate measuring portion 16 is represented by the following equation (18):

$$T_{F16} = l_{16}/V_{23} = l_{16}/(V_s \pm \Delta V_s + v_{16}) \quad (18)$$

where: $\pm \Delta V_s$ is the difference in propagation velocity of the ultrasonic wave between the inlet 15 and the outlet 16 flow-rate portions due to differences in temperature and concentration of the receiving solvent between these portions 15 and 16.

A time $T_F$ for the ultrasonic wave issued from the ultrasonic vibrator 19 to pass through both the inlet 15 and the outlet 16 flow-rate portions of the apparatus is represented by the following equation (19):

$$T_F = T_{F15} + T_{F26} + T_{F16} \quad (19)$$

where: $T_{F26}$ is a time taken for the ultrasonic wave to pass through the partition 26.

On the other hand, in case that the ultrasonic wave issued from the ultrasonic vibrator 20 passes through the inlet 15 and the outlet 16 flow-rate measuring portions of the apparatus of the present invention, the time $T_{R16}$ needed for the ultrasonic wave to pass through the outlet flow-rate measuring portion 16 is represented by the following equation (20):

$$T_{R16} = l_{16}/V_{24} = l_{16}/(V_s \pm \Delta V_s - v_{16}) \quad (20)$$

In the same manner as above, the time $T_{R15}$ needed for the ultrasonic wave to pass through the inlet flow-rate measuring portion 15 is represented by the following equation (21):

$$T_{R15} = l_{15}/V_{22} = l_{15}/(V_s + v_{15}) \quad (21)$$

As a result, the time $T_R$ needed for the ultrasonic wave to pass through both the inlet 15 and the outlet 16 flow-rate measuring portions is represented by the following equation (22):

$$T_R = T_{R16} + T_{R26} + T_{R15} \quad (22)$$

Based on the equations (19), (22) and the fact that the $T_{R26}$ is equal to the $T_{F26}$, it is possible to obtain following equation (23) through with the difference $\Delta T$ in time needed for the ultrasonic wave to pass through the inlet 15 and the outlet 16 flow-rate measuring portions can be calculated:

$$\Delta T = T_R - T_F = T_{R16} + T_{R15} - (T_{F15} + T_{F16}) \quad (23)$$

In the outlet flow-rate measuring portion 16 of the apparatus of the present invention, the flow velocity of the receiving solvent increases by the amount of $\Delta v$ due to addition of the ultrafiltrate produced in the hemodialyzer, so that: $v_{16} = v_{15} + \Delta v$, which is substituted into the equations (18), (20) and is further substituted into the equation (23) into which are also substituted the equations (17), (21) to obtain the following equation (24):

$$\Delta T = l_{16}/(V_s \pm \Delta V_s - v_{15} - \Delta v) + l_{15}/(V_s + v_{15}) - (l_{15}/(V_s - v_{15}) + l_{16}/(V_s \pm \Delta V_s + v_{15} + \Delta v)) \quad (24)$$

Since the $l_{15}$ is equal to the $l_{16}$, they can be represented by the same character "l", so that the equation (24) can be transformed into the following equation (25):

$$\Delta T = l\,((2V_s \pm \Delta V_s - \Delta v)/(V_s \pm \Delta V_s - v_{15} - \Delta v)(V_s + v_{15}) - (2V_s \pm \Delta V_s + \Delta v)/(V_s - v_{15})(V_s \pm \Delta V_s + v_{15} + \Delta v)) \quad (25)$$

In the equation (25), since any of $\pm \Delta V_s$, $\Delta v$ and $v_{15}$ is too small relative to the $V_s$, it is negligible in any of denominators of the items appearing in the equation, so that the equation (25) can be transformed into the following equation (26):

$$\Delta T = l(2V_s \pm \Delta V_s - \Delta v - (2V_s \pm \Delta V_s + \Delta v))/V_s^2 = -(2 \cdot l \times \Delta v)/V_s^2 \quad (26)$$

Consequently, based on the equation (26), it is possible to calculate the increment $\Delta v$ of the flow velocity of the receiving solvent since the $\Delta T$ can be measured, which makes it possible to obtain the amount of the ultrafiltrate produced in the hemodialyzer since the cross-sectional areas of the inlet 15 and the outlet 16 flow-rate measuring portions of the apparatus of the present invention are known. The method for determining the concentration of the receiving solvent in this embodiment shown in FIG. 3 is the same as that described in the above embodiment shown in FIG. 2.

Incidentally, the present invention is not limited to hemodialysis in this application. It is applicable to any other measurement of flow rate and concentration of various fluids.

What is claimed is:

1. An apparatus for measuring an amount of ultrafiltrate produced in a hemodialyzer and a concentration of a receiving solvent employed in the hemodialyzer, comprising:

an inlet flow rate measuring means provided with an essentially vertical input flow channel having two opposing ends, said input flow channel having a first entrance for fluid connection to a supply of a receiving solvent, and a first exit, above said entry port, for fluid connection to an inlet port of a hemodialyzer having an inlet port and an outlet port;

an outlet flow rate measuring means, provided with an essentially vertical output flow channel having two opposing ends, essentially parallel to said input flow channel, said output flow channel having a second entrance for fluid connection to said outlet port of said hemodialyzer and, above said second entrance, a second exit for the exit of receiving solvent from the outlet flow channel after passage through said hemodialyzer and said second entrance;

a first ultrasonic vibrator at one end of said input flow channel for propagating a first ultrasonic wave from said one end of said input flow channel to the other end;

a second ultrasonic vibrator at one end of said output flow channel for propagating a second ultrasonic wave from said one end of said output flow channel to the other end, in the same direction as that travelled by said first ultrasonic wave in said input flow channel;

reflecting means positioned at the ends of said input flow channel and said output flow channel opposite said first and second ultrasonic vibrators, including means for reflecting said first ultrasonic wave into said output flow channel in a direction opposite that of said second ultrasonic wave therein and means for reflecting said second ultrasonic wave into said input flow channel in a direction opposite that of said first ultrasonic wave therein;

first detecting means for detecting said reflected second ultrasonic wave, positioned at the same end of said input flow channel as said first vibrating means; and, second detecting means for detecting said reflected first wave positioned at the same end of said output flow channel as said second ultrasonic vibrator.

2. A device for hemodialysis comprising the apparatus of claim 1, and further comprising a hemodialyzer having an inlet port connected to said first exit and an outlet port connected to said second entrance.

3. The apparatus of claim 1, wherein said input flow channel and said output flow channel are symmetrically with respect to each other about a parallel plane and of and of essentially the same dimensions.

* * * * *